United States Patent [19]

Weichman et al.

[11] Patent Number: 5,615,777
[45] Date of Patent: Apr. 1, 1997

[54] EGG CANDLING SYSTEM

[75] Inventors: Frank L. Weichman, Edmonton, Canada; Jelle van der Schoot, Aalten, Netherlands; Daniel J. Kenway, Edmonton, Canada; Alan J. Hughes, Edmonton, Canada; Carl S. Flatman, Edmonton, Canada

[73] Assignee: FPS Food Processing Systems, Barneveld, Netherlands

[21] Appl. No.: 373,158

[22] Filed: Jan. 17, 1995

[51] Int. Cl.⁶ .......................... A01K 43/04; G01N 21/00
[52] U.S. Cl. .......................... 209/511; 209/579; 209/938; 356/53; 356/237; 250/224; 250/559.22; 250/559.48
[58] Field of Search .................. 209/510, 511, 209/576, 579, 587, 938; 356/52, 53, 237, 355; 250/221, 222.1, 223 R, 233, 224, 559.03, 559.42, 559.48, 559.22

[56] References Cited

U.S. PATENT DOCUMENTS

| 3,210,546 | 10/1965 | Perron | 356/237 X |
| 4,009,965 | 3/1977 | Pryor | 356/355 |
| 4,161,366 | 7/1979 | Bol et al. | 356/56 |
| 4,182,571 | 1/1980 | Furuta et al. | 356/53 |
| 4,240,750 | 12/1980 | Kurtz et al. | 356/237 X |
| 4,487,321 | 12/1984 | Bliss | 209/510 |
| 4,872,564 | 10/1989 | van der Schoot | 209/511 |
| 5,030,001 | 7/1991 | vande Vis | 250/223 R X |

FOREIGN PATENT DOCUMENTS

| 927965 | 6/1973 | Canada . | |
| 373261 | 6/1990 | European Pat. Off. . | |
| 251866 | 8/1992 | Germany . | |
| 6211544 | 9/1987 | Japan | 356/53 |
| 6337245 | 2/1988 | Japan | 356/237 |
| 8303804 | 6/1985 | Netherlands . | |

OTHER PUBLICATIONS

Advance Systems Worldwide article entitled "Crack Detection" published May 1994, author: J. Hordijk. Date written: Jan. 15 1991.
An article entitled "Crack Detection"(Scheur–detector) dated Oct. 12 1978. A copy is enclosed, no author given.
"Investigation of Egg Faults and Methods" Dated Dec. 28 1983. Author, M.G. Schreuder.
Article "A System Approach to Solving Shell Egg Damage Problems" Published in Verslag Berspreking Jan. 1984 by Prof. A.K. Birth.
Paper given by V.C. Humberstone, N.M. Goy, A. VanAsseldonk, J. Hordijk, Jelle van der Schoot, J.M.J. Timmermans, M.G. Scheurder and Tj. J.F. Enzing at Verslag Bespreking. Copy enclosed.
Article "Laser Scanning System for the Automated Inspection of Eggs for Hair Cracks" Published in 1976–1977 by J. Bol.

Primary Examiner—William E. Terrell
Assistant Examiner—Tuan Nguyen
Attorney, Agent, or Firm—Jane Parsons

[57] ABSTRACT

A light beam such a laser beam is used to scan the surface of an egg for flaws such as pin holes, cracks, thinned shell regions, etc. The light beam is vibrated with a rocking/rotating movement to describe a closed curve such as a circle, ellipse or an ellipse so narrow that it is effectively a straight line. The utilization of such a light beam allows identification of types of flaws due to the character of the progression of light emanating from the egg. The invention includes apparatus for rotating the egg about its longitudinal axis in the path of the beam or beams. The apparatus also includes apparatus for forming the vibrating beam such as mirrors vibrated by out of phase electro-magnetic vibration or piezo electric actuators.

32 Claims, 18 Drawing Sheets

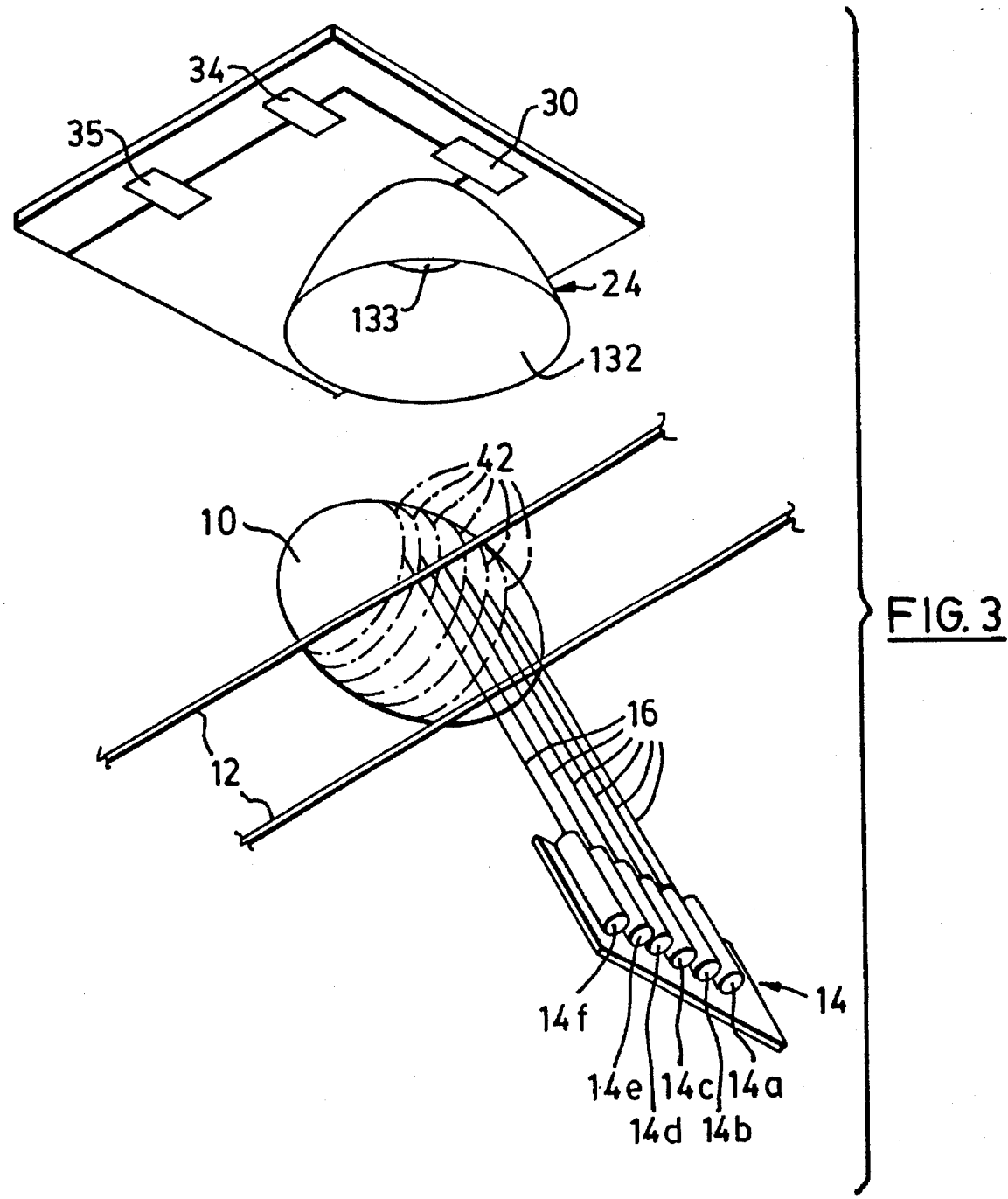

EGG CANDLING SYSTEM

BACKGROUND OF THE INVENTION

1. Field of the Invention

This invention relates to a system and process and apparatus for the detection of flaws in eggs.

2. Description of the Prior Art

Modern, high speed, egg grading packing machines handle up to 40,000 eggs per hour. This number of eggs causes considerable problems in their inspection for hair cracks and other flaws. Although a large number of automatic inspection devices have been proposed, candling of eggs still tends to be by human inspectors by examination in a light compartment. When the number of eggs is large, the number of inspectors must also be large and design of the candling chambers is therefore difficult. Moreover, there is an upper limit to the accuracy and speed at which the inspectors can operate because of the concentration required. Fatigue is a major factor. Thus, one disadvantage of this method for the detection of flawed eggs, is that the expenditure at personnel is relatively high and that, moreover, in practice only about half of the flawed eggs are discovered.

Various automated systems that have been tried include tapping of eggs so that a flaw can be recognized from the type of sound which develops from the tapping, (see for example, Canadian Patent No. 927,965 issued Jun. 5, 1973 to Bliss). Alternatively the change in elastic characteristics can be noted by tapping with a small hammer which bounces back less far from places which are not cracked, (see for example Dutch Patent Application No. 286,485). If an egg is vibrated, a damping of the vibration on the flawed places can be detected.

Examples of previous patents or patent applications which have attempted to solve the problems are as follows:

East German Application No. 293,340, published Aug. 29, 1991 disclosed utilizing the intensity of light transmitted through eggs as a criterion to distinguish between flawed and perfect eggs.

European Patent Application No. 373,261, published Jun. 20, 1990, disclosed locating the eggs on a conveyor roller track at high speed while examining them by a detector. Flawed eggs are discharged from the conveyor at a appropriate position downstream of the inspection station. European Patent Application No. 373,261 is assigned Staalkat BV.

Dutch Patent Application No. 8,303,804, published Jun. 3, 1985 and assigned to Vulcaan BV provides a system for alleviating operator eye strain.

U.S. Pat. No. 4,487,321, issued Dec. 11, 1984 to Bliss, utilizes an elongated pointer for movement into and out of engagement with eggs. Signal generators respond to pointer movement for generating signals for identifying the position of selected articles when they are engaged by the pointer.

U.S. Pat. No. 4,182,571 issued Jan. 8, 1980 to Furuta et al, utilizes light reflection signals obtained from light beams passed through an egg to select blood containing eggs.

U.S. Pat. No. 4,161,366 to Bol et al and issued Jul. 17, 1979, utilizes a laser as a light source to scan the egg. The intensity of light penetrating into the egg is measured. The light penetrating into the egg is partly diffusively reflected, partly absorbed while entering the shell particularly in the case of brown egg shells. Another part of the light gets inside the egg and is strongly scattered by the shell structures. This latter light is dissipated by multiple reflections of the inner surface of the shell and of the yoke sac. The egg glows uniformly. The light radiating from the egg corresponds to the structure of the shell. In particular, the egg shines more brightly when the scanning light beam falls on thin, glassy spots of the shell or an cracks. An actual flash of light may be observed.

The process and system of the invention of U.S. Pat. No. 4,161,366 is of considerable interest in the potential automation of egg candling. However, the characteristic flash of light produced by the process is produced not only by cracks but also by pin holes and regions of thin shell such as cage marks or body checks. Some of these flaws may be acceptable but actual open cracks never are. It is therefore, important to distinguish between cracks and other flaws.

In order to devise a system which will operate in real time at the speeds of the egg handling equipment, it is necessary to be able to distinguish between cracks and other flaws very fast.

The present inventors have addressed the problem of distinguishing cracks from other flaws.

SUMMARY OF THE INVENTION

Accordingly, the invention provides a process for detecting flaws in an egg shell and deducing their nature, comprising the steps:

a) rotating the egg about its longitudinal axis;

b) forming at least one vibrating light beam to describe a geometric figure selected from a closed curve;

d) scanning the egg along at least one circumferential path about the egg in at least one revolution of the egg with said at least one vibrating light beam such that sequential geometric figures of the light beam overlap one another along the circumferential path;

e) detecting and measuring a number of high intensity values of light emanating from the egg during each description of the geometric figure of the light beam; and f) deducing from the number character of high intensity values the nature of any flaws which are present.

The vibrating light beam may be formed by first forming a focused light beam and then vibrating it or by simultaneously forming the beam and vibrating it.

The closed curve may be a circle, an ellipse or an ellipse so narrow that it is effectively a straight line. For example, if during the description of the circle of the focused light beam, the light emanating from the egg does not peak in intensity, then the light beam has not detected a flaw during description of that circle. The number of high intensities is zero and no flaw is recognized.

The speed of rotation of the light beam and the speed of rotation of the egg are such that each circle or ellipse or lime shape described by the light beam overlaps that previously described. (for simplicity of description these circles or ellipses or lime shapes will be referred to herein as "circles" except where particular characteristics of elliptical movement are being discussed). When a circle falls on a crack in the egg across its diameter, two high intensity values will be noted, spaced apart by the diameter of the circle. Previous and succeeding circles will also fall on the crack but, due to the rotation of the egg, the crack will not be diametrical in either the previous or succeeding circle but will be on a chord of the circle. This the high intensity peaks will be closer together. From this information an appreciable amount of information can be deduced concerning the character of the crack.

If, during description of the circle, the light beam indicates one peak in intensity of transmitted light, a flaw is noted but it is possible that this flaw could be a pin hole.

If the peaks are sharp and narrow in character, the actual cracks or pinholes may be involved. If the peaks are wider then thinning of the egg shell may be a possibility. Thus it may be appreciated that different flaws are indicated by different "signatures" of peaks. This will be discussed more fully with reference to the drawings.

The invention includes apparatus for detecting flaws in an egg shell and for deducing their nature, the apparatus comprising:

a) means to rotate the egg about its longitudinal axis;

b) means to form at least one vibrating beam of light to describe a geometric figure selected from closed curves and straight lines;

d) means to direct the at least one light beam to scan the egg along at least one circumferential path thereabout during at least one revolution of the egg with said at least one vibrating light beam such that sequential geometric figures of the light beam overlap one another along the circumferential path;

e) detection means to detect peaks in intensity in light emanating from the egg;

f) signal processing means to develop a progression of signals corresponding to the number, size and character of said peaks in intensity of said light emanating from the egg;

g) computer means to process said signals and to deduce, from the number, size and character of the peaks in intensity, the nature of a flaw in the egg.

The apparatus may include means to rotate the egg about its longitudinal axis comprising a preliminary conveyor having spool rollers to impart preliminary spin to the egg and a secondary conveyor having means to increase the preliminary spin to a prechosen designed spin speed. The secondary conveyor may include a ramp down which the eggs roll and driven support strings for the egg longitudinal of the ramp to impart spin to the eggs through friction with said strings.

The computer may include at least one digital signal processor for each egg. It may be programmed with comparative data for peaks of light intensity characteristic of specific types and shapes of flaws. These "signatures" may be used for instant identification of such flaws without the need to make full calculation of each flaw.

The means to vibrate the focused light means may be a vibrating mirror which may also serve the purpose of directing the light beam to scan the suitable circumferential band of the egg. The mirror may be vibrated using piezo elements to produce a rotary rocking motion. Alternatively, the light beam could be moved by multiple spinning mirrors or by electromagnetically excited spring piezo electric elements.

The light beam itself may be produced a laser. Conveniently, the laser may be an HeNe laser or a solid state semi conductor laser.

For eggs of normal size it may be preferred to scan six or even more circumferential bands. For small eggs, four or five circumferential bands may be sufficient and for large eggs it is contemplated that more than six bands would be required. Each band may, as stated, be the width of the diameter of the circle described by the laser beam. This diameter may be in the region of 2 mm although diameters of less than 2 mm or more than 2 mm are also possible.

The number of laser beams may correspond to the number of circumferential bands on the egg. A laser beam may scan one circumferential band in one revolution of the egg and another circumferential band in another revolution of the egg. The choice of which bands are scanned may be a set pattern which may be altered if particular emphasis on a region of the egg is desirable due, for example, to the need to obtain further information as to the nature of a flaw.

The laser beam should be focused to produce a light spot of suitable size. Spot sizes from 20 microns to 2,000 microns may be possible but a spot size of 200 microns may be generally suitable. This may be achieved utilizing a 100 mm focal length lens.

The frequency at which the laser beam draws circles, ellipses or other figures, may vary from 100 Hz to 20,000 Hz, but typically a frequency of 20,000 is suitable.

The speed of rotation of egg rotation may be varied within quite wide limits. A rotation of from 2 rps to 5 rps easily accommodated within the parameters of the system. Even speeds up to 10 rps may be possible.

If six circumferential bands are to be scanned on each egg it may be necessary to utilize six separate laser beams. This movement and the rotation of the laser beam so that its focused spot describes a circle on the egg may be achieved utilizing a single vibrating mirror for each beam so that the beams are manipulated in the same manner. Alternatively, this may be achieved using multiple high speed spinning or rocking mirrors. The speed of spinning or rocking may be, for example, from 20,000 rpm to 120,000 rpm.

The incident optical system, therefore, comprises a number of lasers, a spinning or rocking mirror or mirrors to otherwise cause beams from the lasers to describe circles, lenses to focus the beams and optionally some protection glass between the lens and the egg. The incident light from the lasers may be directed from below onto eggs being transported by egg candling equipment. Rollers or strings of the candling equipment are arranged to rotate the eggs about their longitudinal axes at an appropriate speed and to allow access of the laser beams. Above the egg candling rollers or strings photo detection apparatus is arranged to detect effects of the laser beams on the eggs. Upstream of the rollers or strings, egg advancing equipment progressively increases the spin of the eggs so that there is no sharp increase of spin speed which might jolt the eggs.

The photo detection may include a large area photo diode and an ellipsoidal reflector approximately 74 mm (one egg size) in diameter with a semi-major axis at comparable dimension is used to gather light. This type of reflector is used in a non-focused mode, since neither the glowing surface of the egg nor the large area photo diode employed are point piezo electric elements.

The detector may be alternatively, for example, a photo multiplier tube.

The photo diode is provided with a band pass filter (like a Schott filter) which only passes light in the appropriate wavelength band matched to the laser source. The photo diodes are large in area, but relatively low in capacitance. For example, a photo diode with an area of 100 $mm^2$ and a capacitor of about 1,500 pf (like the UDT PIN 10 PI) would be suitable.

The signal from this photo diode needs to be amplified by a high gain, ultra low noise, broad band transconduction amplifier with DC blockings.

Such a photo detection amplifier might have characteristics as follows:

| | |
|---|---|
| Gain pass band | 100 Hz to 200 Hz |
| Fluctuations equivalent to input noise | 30,000 photons or fewer per 10µ sec time period |
| Wave length of peak sensitivity | 685 nm |

The defect detection may comprise a DSP detector capable of discriminating the sharp pulses generated by entry of the light into a flaw. These sharp pulses need not necessarily be of high amplitude.

The digital signal is entered into a computer having a program to calculate, from the signals, the presence of the defect and its type. The characteristics of a "detected crack" versus a "other defect" are well determined by the trajectory/spot size combination. If a 2 mm trajectory (6300 micron circumference) is used with a spot size of approximately 250 microns, the transit time for a small crack of less than 50 microns at a scan frequency of 2000 Hz the signature for a crack will be:

$$\frac{250}{6300} \times \frac{1}{2000} = 20 \text{ micro seconds}$$

Since the crack is two dimensional, it may be traversed twice in a 2 mm circular trajectory. Therefore, the fundamental criterion for detecting cracks versus more diffuse defects like body checks is that the peaks from cracks are much more shorter in duration.

The fundamental criterion for detecting cracks versus point defects like pin holes, is the cracks will have two "hits" within every laser loop while in pin holes (unless they are multiple and improperly clustered) will have only one.

It is occasionally possible that pin holes will line up so as to produce the pair of thin pulse signature associated with cracks. True crack signatures can be distinguished because they are associated with a "progression" as the circle moves across the crack. A real crack shows a clear progression involving two sharp narrow peaks.

A cage mark is distinguishable since the peaks associated with the cage marks are either broader, of lower amplitude, or both.

The apparatus for defect detection and distinguishing of flaw type may be utilized with standard egg handling machinery. Such standard egg handling machinery may transport the eggs on rollers in one or more rows, six rows of eggs may be used for example. Conveniently, the focused laser beams may be directed towards the circumferential bands on the eggs from below. The laser beams may be arranged to shine between rollers, belts and strings to access the eggs. The photo detection apparatus may be located above the conveying rollers and the eggs to receive light transmitted from them.

BRIEF DESCRIPTION OF THE DRAWINGS

An embodiment of the invention will now be described by way of example with reference to the drawings, in which:

FIG. 3 is a schematic view of an egg showing six parallel scanning bands thereon;

DETAILED DESCRIPTION OF A PREFERRED EMBODIMENT

Figure 1:
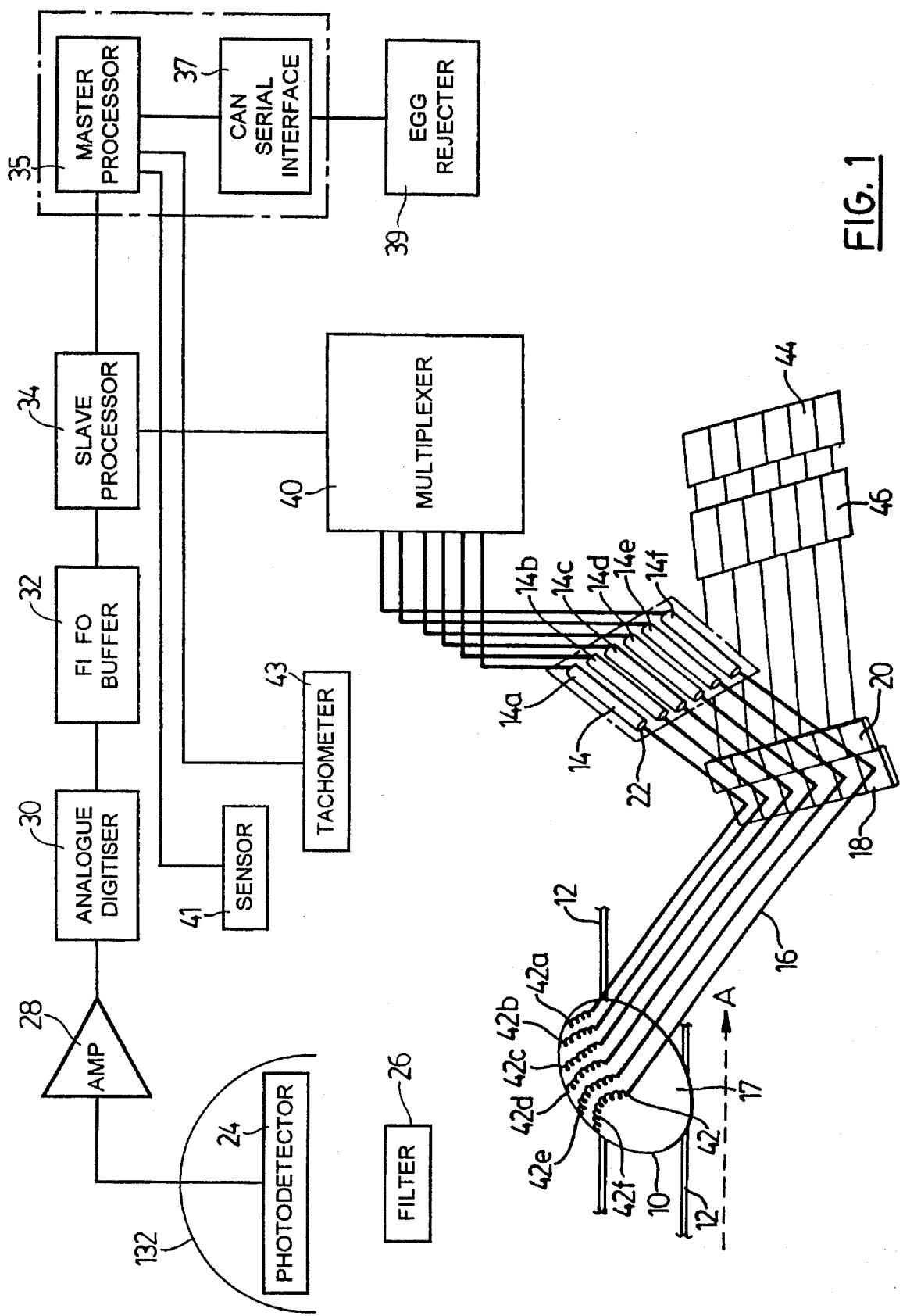
FIG. 1 is a simplistic schematic block diagram of one exemplary set up arrangement.

FIG. 1 shows an egg 10 of a line of eggs being spun. The egg is one of a line of eggs being transported in the direction of arrow A.

The egg 10 is rolled on a pair of narrow rollers or strings 12 so that it can be spun at high rate. The egg 10 may spin about its longitudinal axis at speeds up to 5 rps while still allowing for unobstructed access for laser beam 16 to its surface. The strings 12 are slightly spaced apart so that the egg may be illuminated from below between the strings.

Illumination is provided by means of a bank of six lasers 14 each one of which provides a beam 16. Each laser beam 16 is reflected by a mirror 18 which is vibrated by a piezo electric element 20. Laser beams 16 are collimated and focused by lenses 22 and reflected from mirrors 18 and reflected to form six discrete circles on the surface of the egg 10. The bank of lasers 14, lenses 22, the mirrors 18 are located so that the focused laser beams fall on the egg from below between the strings 12.

Above the egg, a photo detector 24, including a wide area photodiode 133 and an ellipsoidal reflector 132, is arranged to receive light transmitted from the egg. The light is focused on the photodiode by the ellipsoidal reflector. A lens could optionally be used. Detected signals 26 are amplified by amplifier 28, digitised by digitiser 30, and passed to digital signal processor 34 via fifo buffer 32 for assessment of the results. Digital signal processor 34 may be a TMS 320C50 DSP or similar signal processor. Thereafter, data is processed by master processor 35 which, through CAN serial interface 37, communicates with egg rejector 39. The rejection 39 is not described in detail since it may be a conventional rejector which may be actuated in response to a rejection signal from the apparatus of the invention. A sensor 41 or a synchronous machine signal senses the presence of each new egg 10 and a tachometer 43 senses the speed of spin on the egg.

As illustrated in FIG. 1 laser bank 14 comprises six separate lasers, 14a, 14b, 14c, 14d, 14e, and 14f, each one of which is multiplexed by multiplexer 40 to scan six circumferential bands 42 on egg 10. One system of operation may be as follows:

Initially, each of the six lasers 14a, 14b, 14c, 14d, 14e and 14f projects its circle onto corresponding circumferential band 42a, 42b, 42c, 42d, 42e, and 42f of the egg 10. They are then switched so that, for example, laser 14a is directed to circumferential band 42b. Laser 14b is directed to circumferential band 42c, laser beam 14c is directed to circumferential band 42d and eventually laser beam 14f is directed to circumferential band 42a.

Only one laser is allowed to illuminate the egg at a time, so that the origin of the detected signature may be known. Ordinarily the lasers switch in rotary sequence 1,2,3,4,5,6,1, etc. However, if more sampling is required to examine a feature of interest, this cycle may be varied, to repeatedly sample and confirm the "progression" in one band. For example, if a pair of thin peaks were detected in the third band the sequence might be varied in real time to 1,2,3,3, 3,4,5,6 . . . etc.

Figure 2:
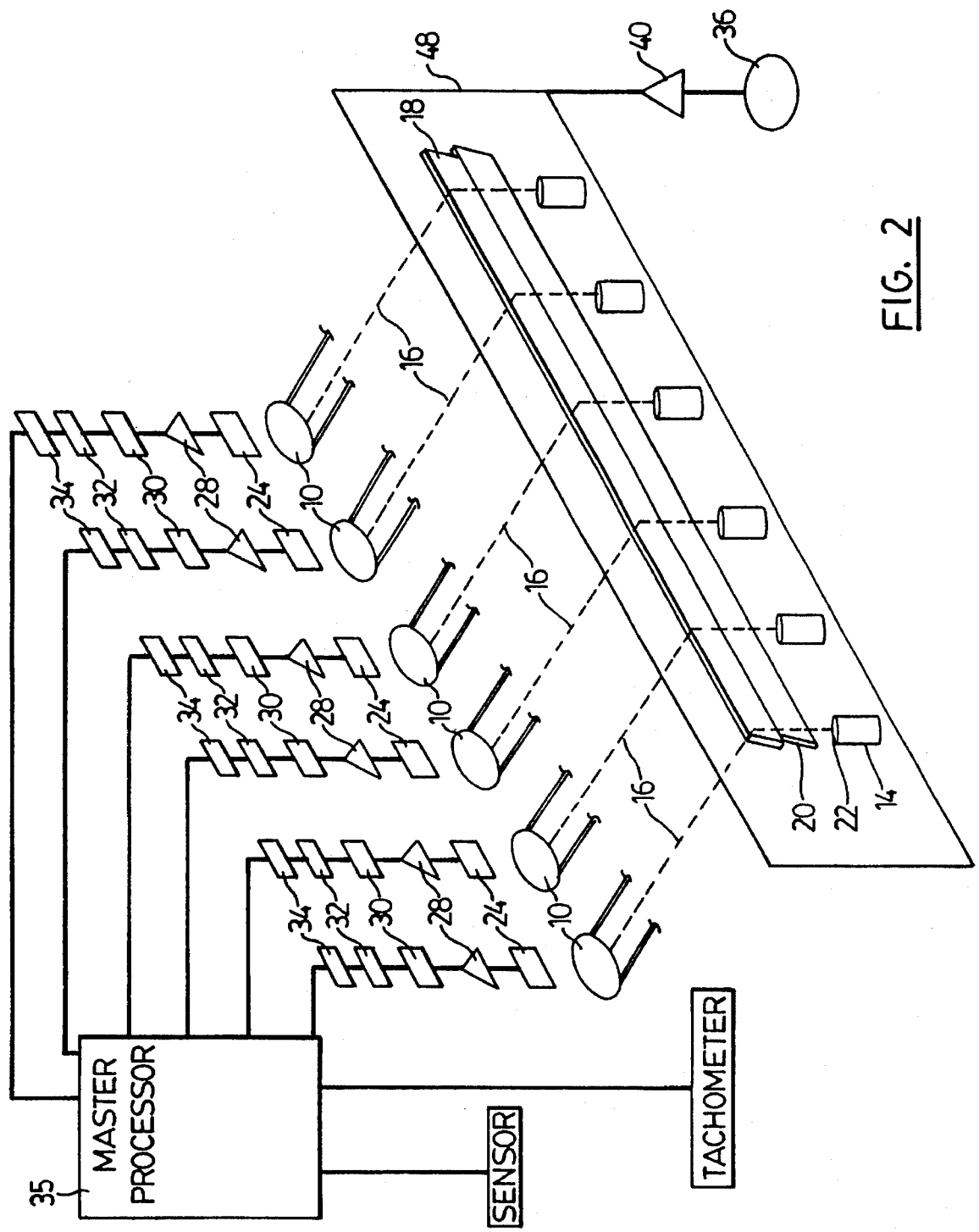
FIG. 2 shows a second simplified block diagram for six rows of eggs.

FIG. 2 shows a system which is extended to a row of six lines of eggs. Each egg of a line of eggs is supported and spun by a pair of strings 12, at least in the region where it is scanned by laser beam 16. Separate pairs of strings 12 for each line of eggs. For each egg 10, photo detector 24, its associated amplifiers, digitisers, and fi fo buffers 32 are provided. Each egg 10 has its own signal processor 34 which may accept signals from the photo detector and output data concerning flawed eggs in accordance with its program.

FIG. 3 shows the photo detector 24 in relation to egg 10 spinning on strings 12 but, for simplicity, without showing any of the general egg handling apparatus such as the hollow rolls 106, ramp 102 etc. The photo detector is an ellipsoidal reflector 132 approximately 74 mm in diameter. A large area photodiode 133 receives light from the reflector and signals are passed to analogue digitiser 30 and from thence to signal processor 34.

The mirror 18 which will be described in detail hereinafter may be a single mirror or may comprise an individual mirror for each laser beam. It may be given a rocking/rotating movement by a piezo electric element 20. While piezo electric element 20 is described it will be understood that any other suitable vibration may be employed. The lenses 22, and lasers 14, may be contained in a single lens box. Indeed, the whole of the incident optical system may be housed in a block housing 48 which is located in a position beneath strings 12. The piezo electric elements may be driven by drivers 46 and wave form generators 44.

The system of FIG. 1 or FIG. 2 operates to scan the surface of each egg as it rotates about its longitudinal axis. To obtain suitable comprehensive scanning of the surface the laser beams may be arranged to scan, say, six circumferential bands 42 about the egg. For eggs about normal size six circumferential bands may be suitable. These may be individually scanned by separate lasers as shown in FIG. 3 or they may be scanned by some other multiplexed arrangement.

The laser beams 16 which have been focused to form an illuminated spot on the surface of the eggs by means of lens 22 may be manipulated by vibrating mirror 18 so that the spot described a small circle on the surface of the egg. The diameter of this small circle corresponds to the width of each band. For a typical egg having a length of 6 cm and a diameter of 4 cm and a circumference of 14 cm, the size of the scanning circle and therefore the width of the circumferential band may be around 2 mm. Suitably there may be six circumferential bands although more than six for large eggs and less than six for small eggs is also possible.

It has previously been noted that the word "circle" is used to include an ellipse except where it is necessary to particularize ellipses. When the laser does not have a 1:1 aspect ratio an ellipse must be chosen as the continuous curve. Moreover, the ellipse chosen must have the same ratio of its major and minor axes as does the laser. If, for example, the lasers of laser bank 14 are semiconductor lasers with a 3:1 aspect ratio, the trajectory shall be an ellipse with the same aspect ratio aligned with the axis of the laser spot.

For the egg illustrated in FIG. 3 the following data may be typical.

Figure 5A:
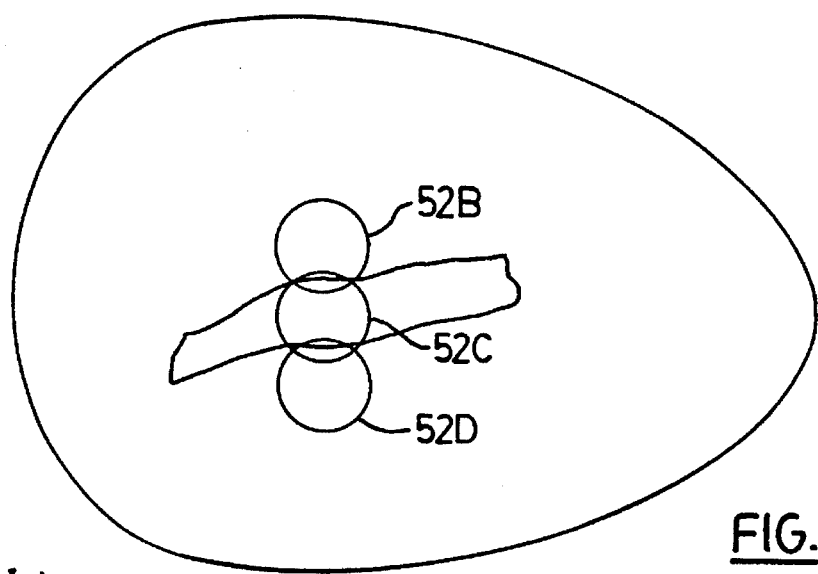
FIGS. 5A, 5B, 5C and 5D show the progress of a laser circle over a thinned area of the surface of an egg and a simplified progression of signals caused thereby.
Figure 5B:
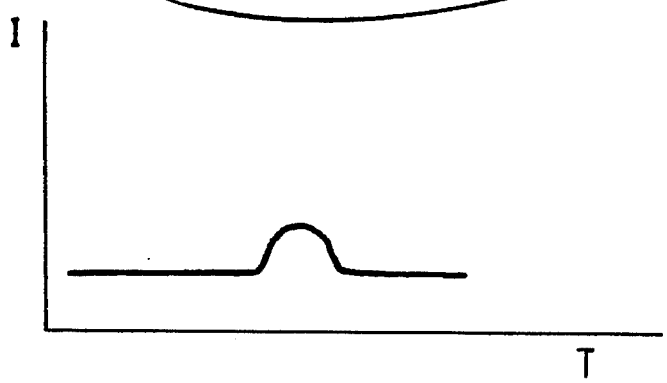
Figure 5C:
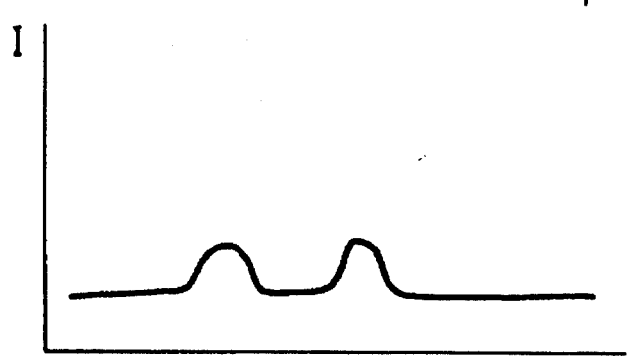
Figure 5D:
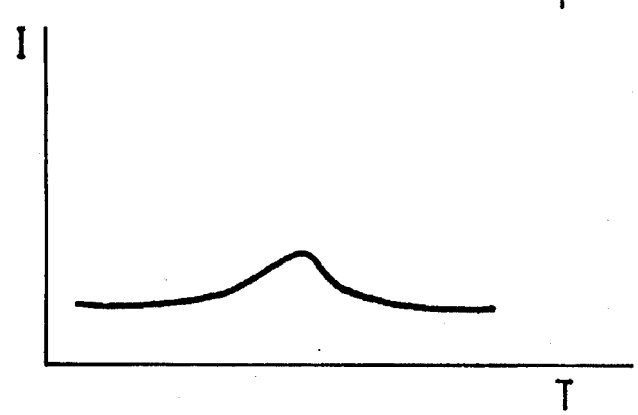
Figure 6A:
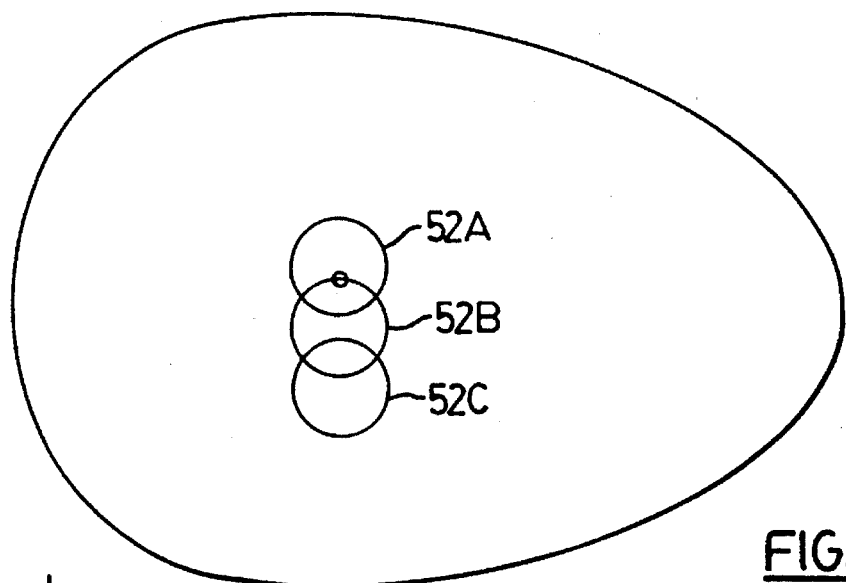
FIGS. 6A, 6B, 6C and 6D show the progress of a laser circle over a pinhole in the surface of an egg and a simplified progression of signals caused thereby.
Figure 6B:
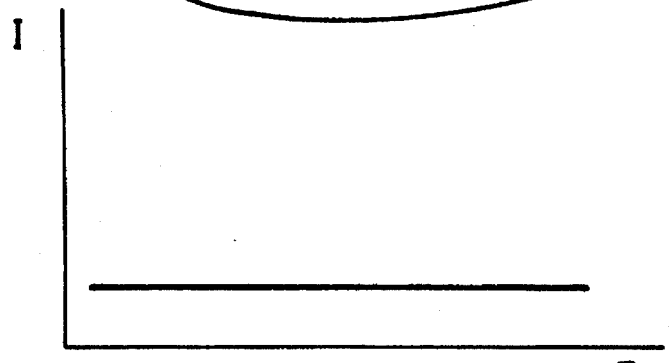
Figure 6C:
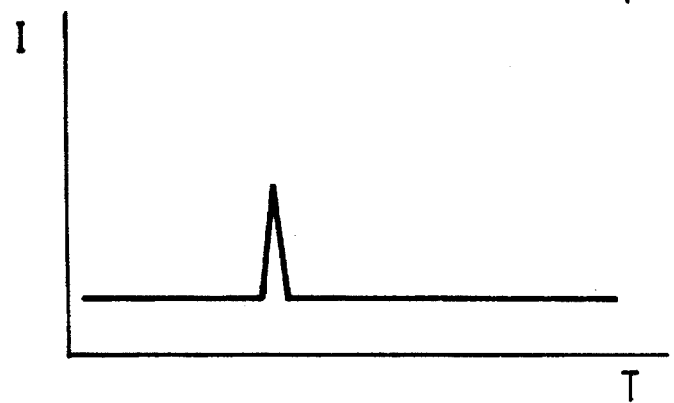
Figure 6D:
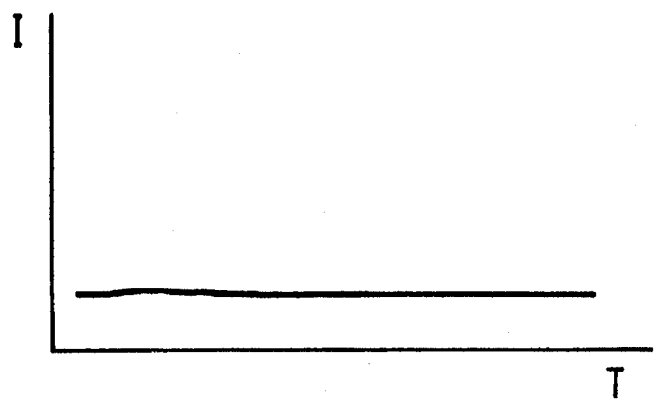

Scanning ellipse size 2 mm on its minor axis and 6 mm on its major axis perpendicular to egg's axis of rotation Repeat rate for circle 2000 HZ Line rate=2000 HZ/6 bands=333 HZ Egg spin rate 4.5 rev/s Egg surface velocity 140 mm/rev×4.5 rev/s=630 mm/s Travel distance per line rate 630 mm/s/333 HZ=1.9 mm Scanning pattern: band of ellipses, each of which overlaps the preceding ellipse at widest part of egg Laser spot size 250 μm Typical crack>10 μm Spot coverage 6300 μm in 2000 fm of a second Spot velocity 6300 μm×2000=12.6 m/s Flash time 250 μm/12.6 m/s=20 μs Sampling rate=2–4 μs Each type of flaw on the surface of egg 10 will have its own particular signature in the signals produced by photo detector 24. The signatures of simple cracks, thinned areas such as cage marks and pin holes are illustrated on the surface of the eggs of FIGS. 4A, 5A and 6A and the progressions which show their signatures are respectively illustrated in FIGS. 4B, 4C, 4D, and 5B, 5C, 5D and 6B, 6C, 6D.

Figure 4A:
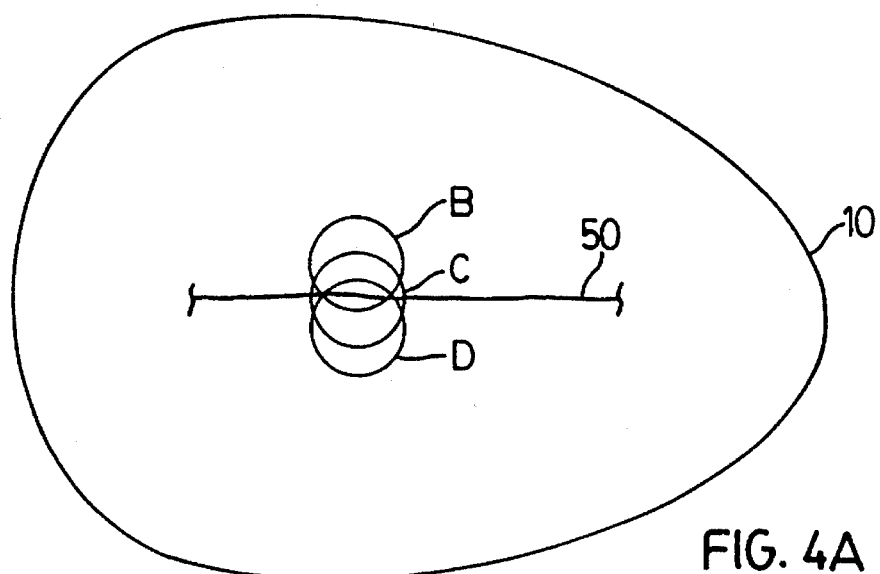
FIGS. 4A, 4B, 4C and 4D show the progress of a laser circle along a circumferential band of the egg over a crack and a simplified progression of signals caused thereby.
Figure 4B:
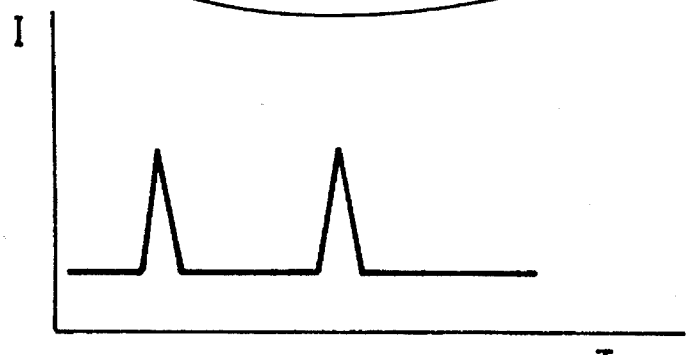
Figure 4C:
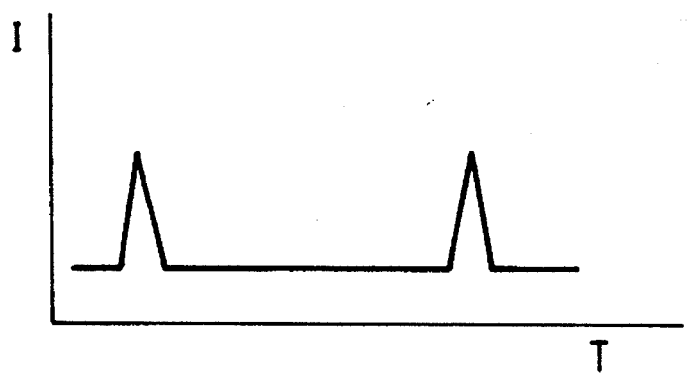
Figure 4D:
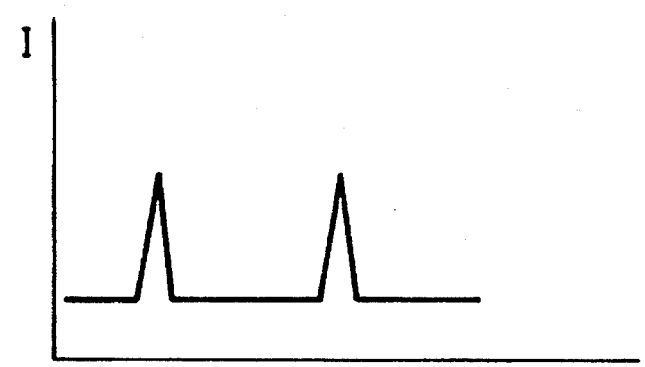

FIG. 4A illustrates an egg 10 having a crack 50. The circles 52b, 52c, and 52d illustrate sequential positions of laser circle 52 on one of the circumferential bands 42. FIG. 4B is a simplified plot showing the light level as a function of time for circle 52b of FIG. 4A. Similarly, FIGS. 4C and 4D are similar simplified plots of the light level as function of time for circles 52c and 52d of FIG. 4A. The actual shape of the peaks showing a sharp narrow large rise indicates an actual hole in the shell. The paired peaks indicate a crack since the circle crosses the crack twice. The progression of FIGS. 4B, 4C, 4D show paired peaks closer together for circle 52b where the crack constitutes only a minor chord of the circle (FIG. 4B), show the paired peaks wider apart for circle 52c, the diameter of the circle (FIG. 4C), and show the paired peaks closer together again for circle 52d when the crack constitutes only a minor chord of the circle again (FIG. 4D).

$$\Delta + \approx \frac{[\text{beam diameter}]}{[\text{circumference of trajectory}]} \times [\text{time required for beam to complete one trajectory}]$$

$$\approx \frac{250 \text{ μm}}{\pi \times 2 \text{ mm}} \times [0.5 \text{ milliseconds}]$$

$$\approx 250\mu \times 500 \text{ μsec}$$

$$\approx 20 \text{ μsec}$$

FIGS. 5A, 5B, 5C and 5D are a similar series of drawings to those of FIGS. 4A, B, C, D but FIGS. 5A to 5D are concerned with an egg 10 having a cage mark or thinned region 54. The thinned region tends to be much wider in character than any physical crack 50. Thus the actual character of the peaks of transmitted light from the cage marks are smaller, wider and not so sharp as those for cracks. For circle 52b where the cage mark constitutes a minor chord of the circle, a single wide blunt peak is obtained. Circle 52c overlaps both edges of the cage mark. Therefore a pair of shallow blunt peaks are obtained for this circle. Circle 52d is moving away from the cage mark and FIG. 5D again shows a single wide peak which is narrower than that of circle 52c. It is especially important to note that ellipses are included within the meaning of the term circle and that in practice an ellipse will almost certainly be used.

$$\Delta + \approx \frac{[\text{beam diameter} + \text{cage mark width}]}{[\text{circumference of trajectory}]} \times$$

[time required for beam to complete one trajectory]

There is no problem distinguishing if the width of the cage mark is greater than 100μ or even less.

FIGS. 6A, 6B, 6C, 6D show a similar series of drawings for a pin hole 56. In this case, only a single peak is shown. It will, however, be appreciated that if the pin holes 56 were clustered by coincidence to produce apparently paired peaks. In this case, the progression would not be similar to that of FIGS. 4B, 4C, and 4D since sequential circles would not cross the pin holes in the same pattern as they would cross the crack 50.

Figure 7:
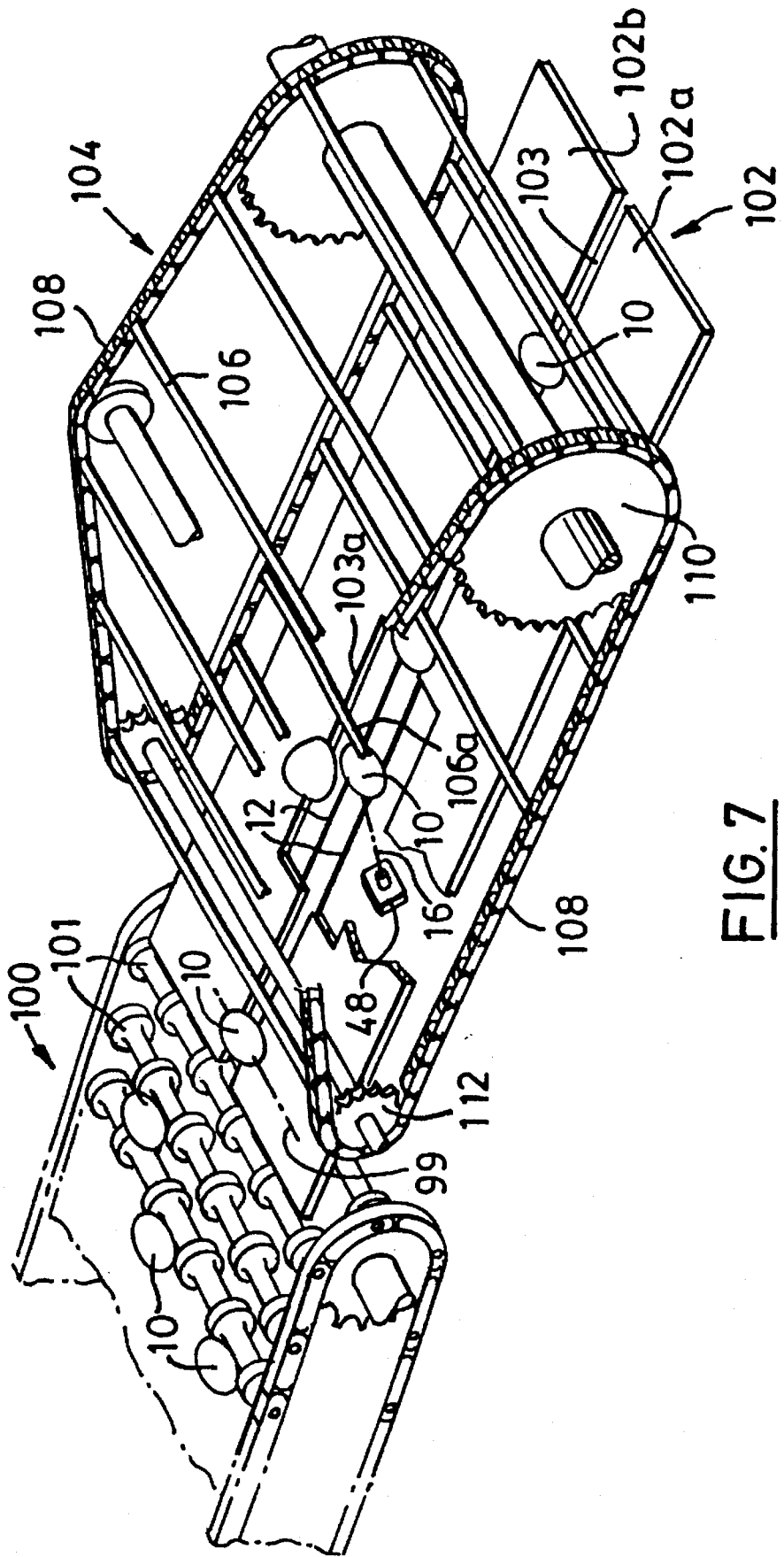
FIG. 7 shows a schematic simplified view of apparatus for according to the invention.
Figure 8:
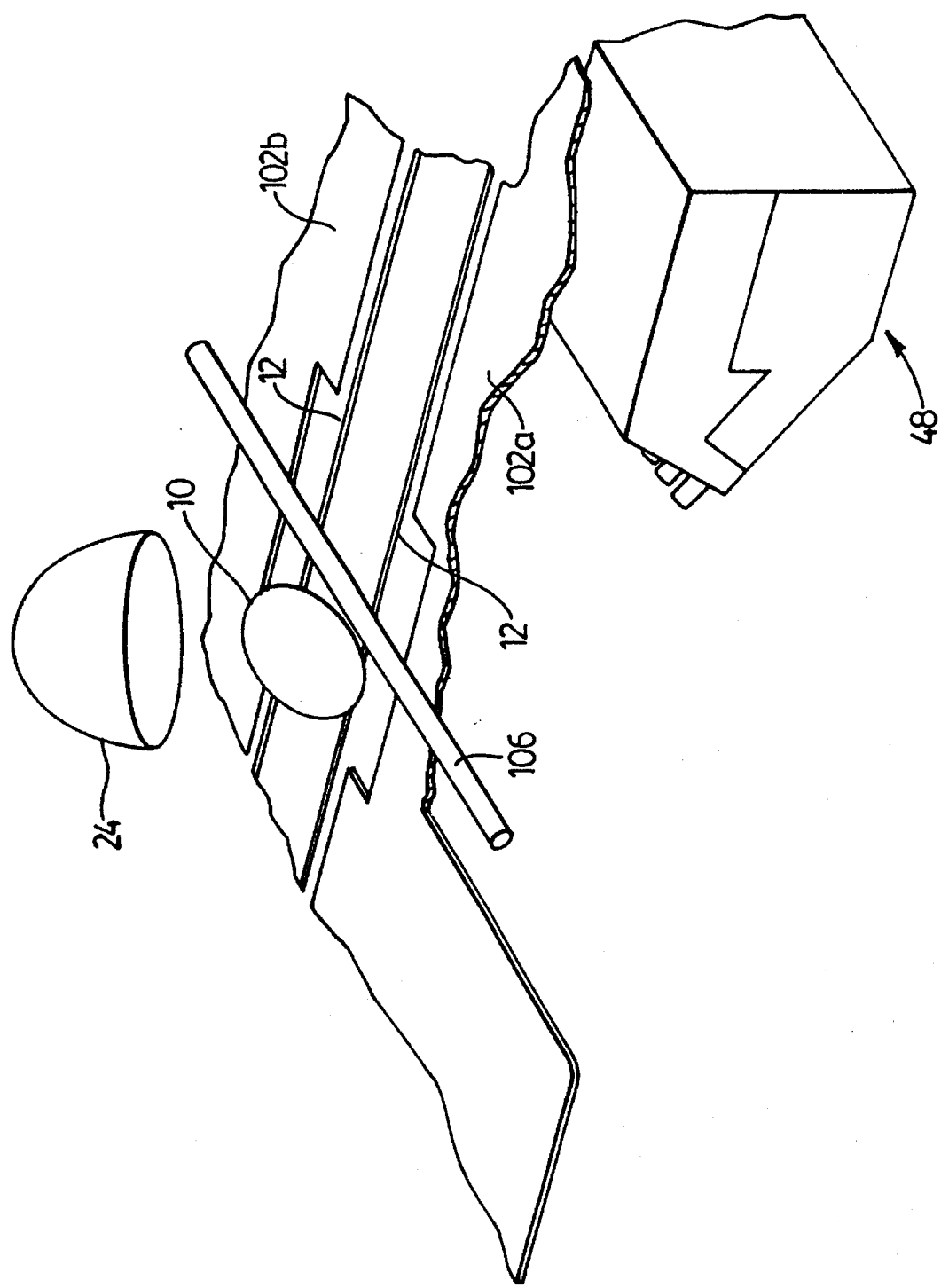
FIG. 8 is a detail of FIG. 7.

The system so far described may be implemented by the apparatus shown in FIG. 7.

Eggs 10 are initially carried on conveyor 100 by independently spool type rollers 101 which builds the spin of the egg about its longitudinal axis shown generally at 100. The rollers 101 rotate thus allowing spinning build up of the eggs. Eggs 10 are then transferred onto a ramp 102. The ramp 102 is tilted downwardly so that the spinning eggs roll down the ramp 102. The ramp 102 comprises two downwardly sloping ramp parts 102a, 102b having a channel 103 therebetween down which the eggs roll.

Means are provided to keep the eggs spaced one from the another in orderly fashion without impeding their spin. This means may be a conveyor 104 comprising hollow rolls 106 extending across the ramp and having their ends engaged in a pair of conveyor belts or chains 108. The hollow rolls 106 are spaced apart sufficiently to space the eggs appropriately. The conveyor belts 108 are rotated to move the hollow rolls down the ramp and return them to an upstream end of the ramp to segregate, space and order the progression of eggs down the ramp. As illustrated the continuous conveyor 104 of hollow rolls of 106 is operated on cog wheels 110 and 112. Upstream cog wheels 112 are much smaller than downstream cog wheels 110. Thus the upper return run of conveyor 104 may be generally horizontal rather than following the downward slope of forward run of conveyor 104 which corresponds to the slope of ramp 102. The hollow rolls 106 may, of course, be replaced by bars but the hollow rolls are believed preferable in having less impedance on the spin of the eggs.

Each egg 10 is restrained from untoward movement down the ramp by the hollow roll 106 immediately downstream of it. As each egg 10 proceeds down the ramp on channel 103, it arrives at a widened channel portion 103a. At the widened channel portion 103a, the egg 10 is wholly supported by strings 12 which are provided longitudinally of the ramp and restrained from rolling forward by hollow roll 106a.

The strings 12 each comprise an endless belt driven at a speed chosen to impart the final spin to the eggs. The strings 12 are spaced apart to carry an egg on them. The movement of strings 12 impart extra final spin to egg 10 to bring it up to speed.

This spin, as previously discussed may be around 4.5 rps to rotate the egg at least one revolution during the laser scan. It will, of course, be appreciated that while 4.5 rps is suitable, spin rates of less than this or more than this are possible. Spin rates of 3 to 5 rps are generally preferred although spin rates up to 10 rps may be achievable.

Strings 12 are spaced wide enough apart and the widened channel portion 103a is large enough to expose a surface of the egg beneath them. This surface is accessed by laser beams 16 from block housing 48 which houses the lasers 14, the mirrors 18 and piezo electric elements 20 or other means to vibrate the beam describe a circle. The block housing 48 and associated multiplexer are illustrated in FIGS. 9A and 9B.

The photo detector 24 is located above the spinning egg 10. Photo detector 24 is only indicated schematically in FIG. 7.

Figure 9A:
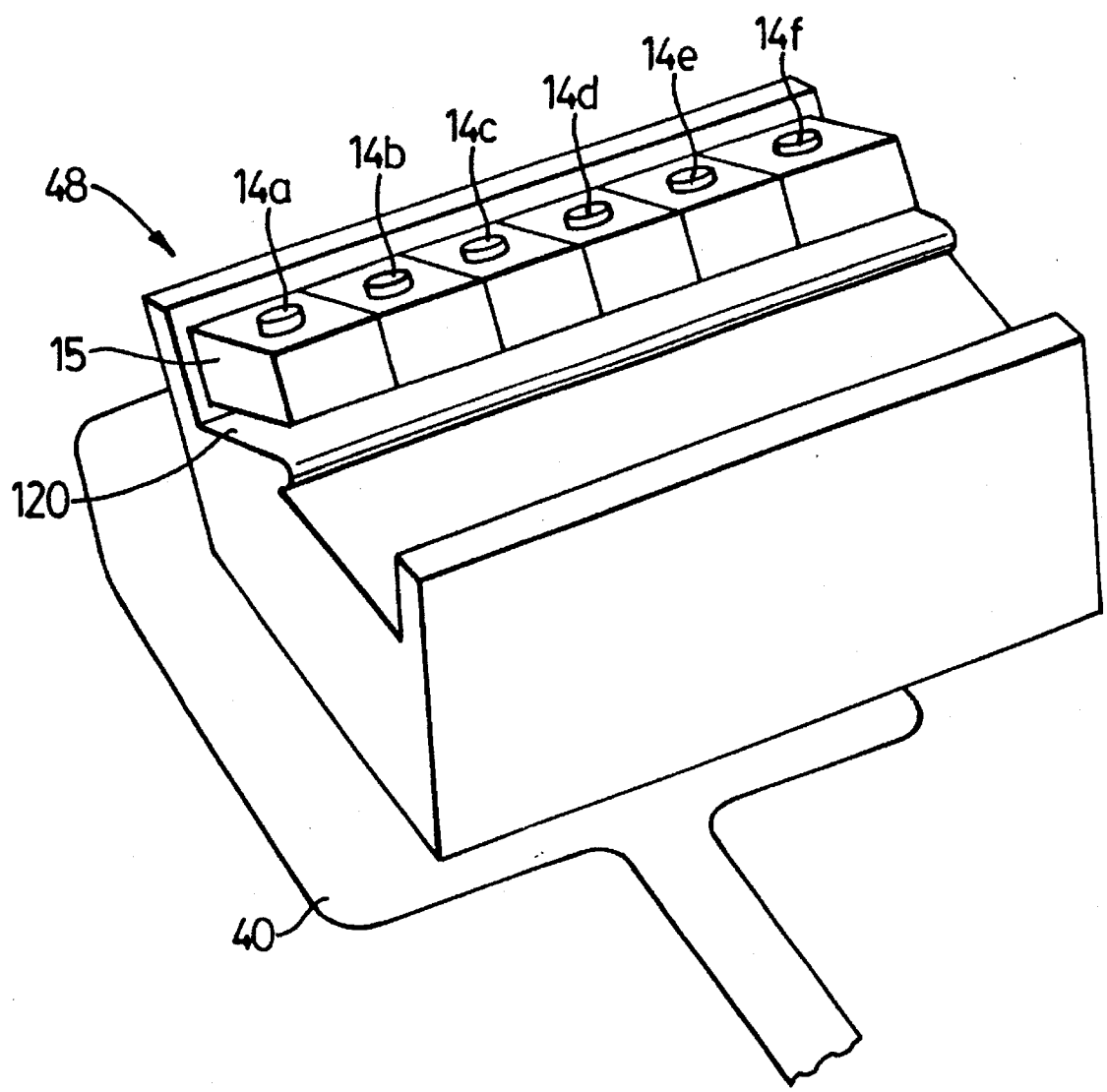
FIGS. 9A and 9B are views and details of the incident optic block.
Figure 9B:
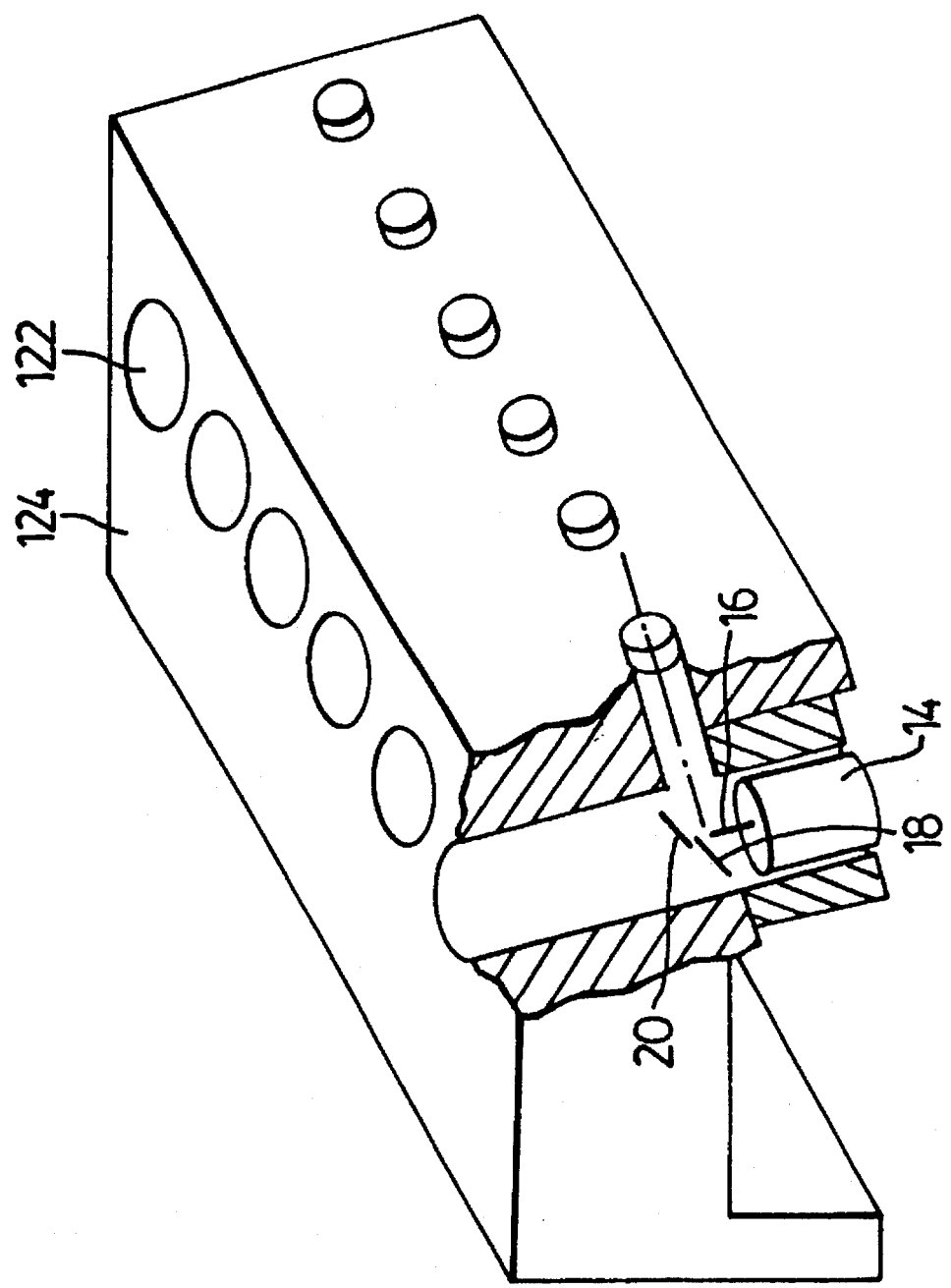

FIG. 9A is a simplified perspective view of a light block housing 48 showing lasers 14a, 14b, 14c, 14d, 14e and 14f housed in blocks 15 located in a recess 120 of block 48. FIG. 9B shows the same block 48 from above, having sockets 122 in a top surface 124 housing mirrors 18a, 18b, 18c, 18d, 18e, and 18f, each associated with a piezo element 20. The mirrors and each laser 14a, 14b, 14c, 14d, 14e and 14f directs its beam onto a respective mirror 18a, 18b, 18c, 18d, 18e, and 18f. The mirrors 18 are manipulated as described by piezo elements 20 to rock and/or rotate to manipulate the laser beam 16 to form a circle. As previously discussed, the circle may be an ellipse. When the circle is an ellipse, the ratio of its major and minor axis should be the same as the aspect ratio of the laser.

The trajectory of the laser beams 16 exits block housing 48 at exit ports 23 in a front sloped surface 122 of housing 48. In the case of semiconductor lasers the primary collimating lenses are located at the front of lasers 14a, 14b, 14c, 14d, 14e, and 14f. In the case of semiconductor lasers, they may be modulated by switching the automatic power regulating circuitry to stabilize the beam output. Each piezo electric element is controlled by an oscillator while amplitude and frequency may be adjusted to control the beam trajectory. A shuttling reflector may also be present in order to keep the laser beam on the egg 10. It will be appreciated that the trajectory shown in FIG. 9B is very simplistic and does not include various additional reflections for directing the beam.

Figure 10A:
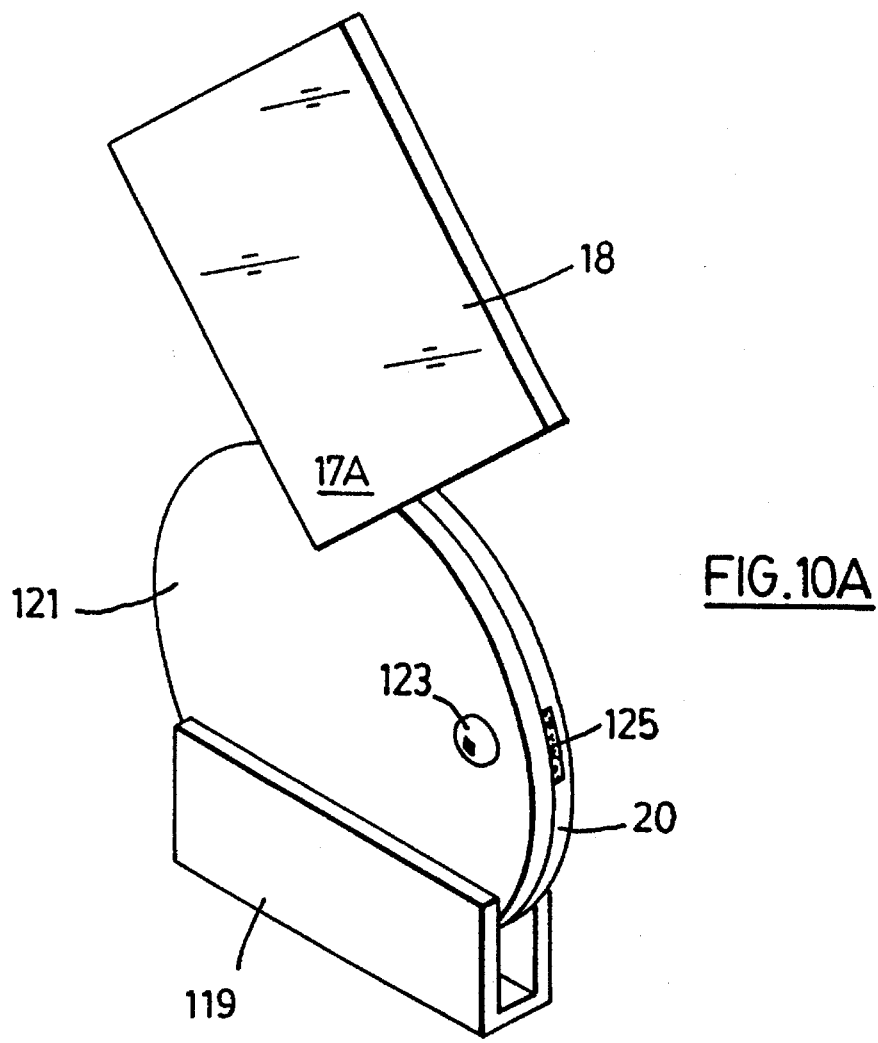
FIGS. 10A, 10B and 10C show alternative embodiments of vibrating mirrors which may be used.
Figure 10B:
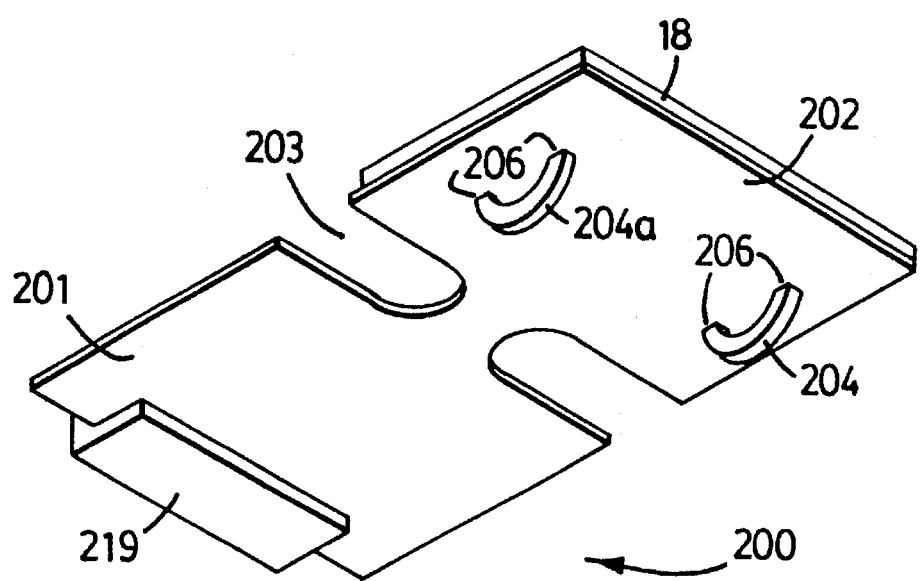
Figure 10C:
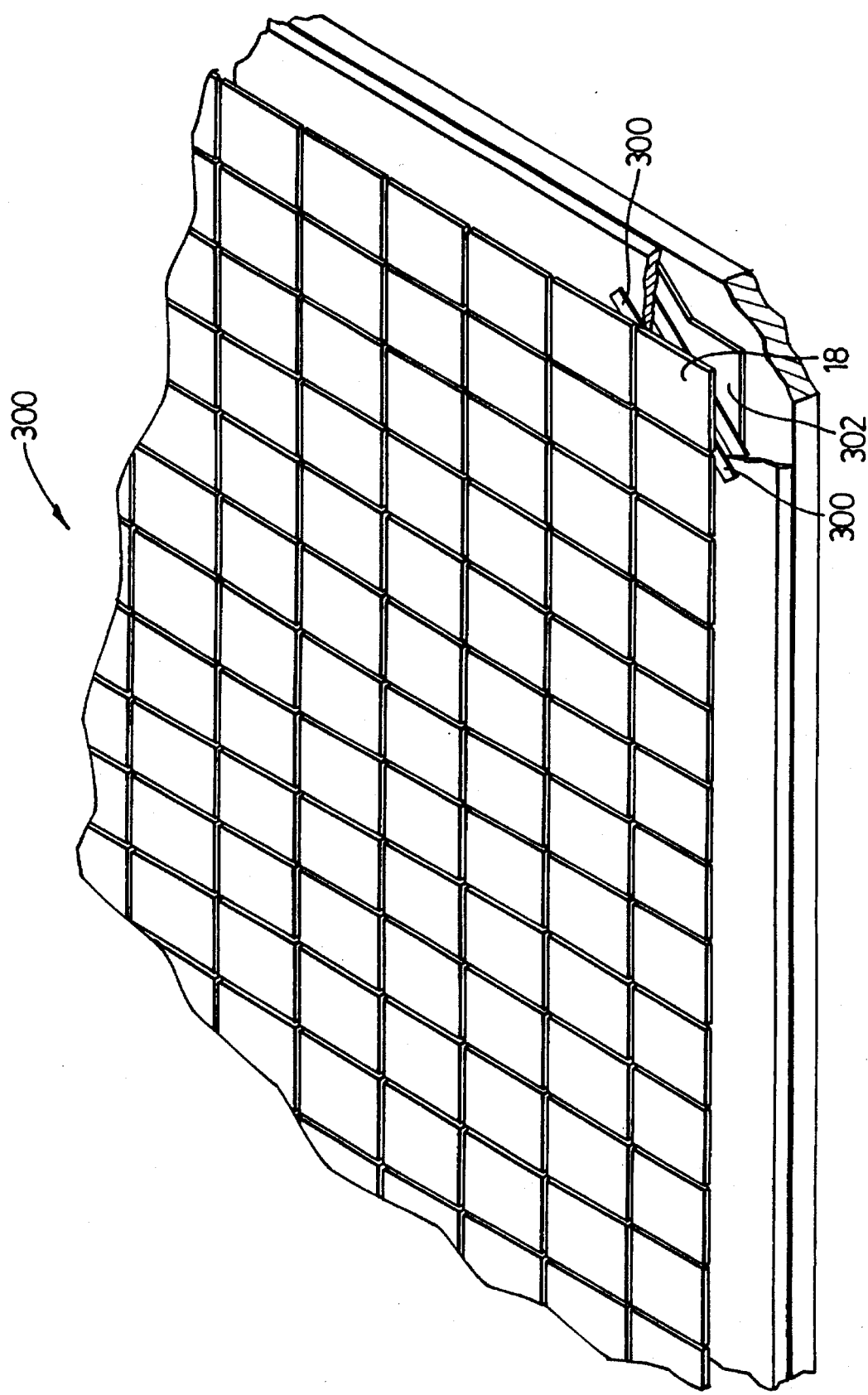

A variety of means for producing discrete beams 16 are shown in FIGS. 10A, 10B, and 10C. FIG. 10A shows an enlarged view of one of the mirrors 18 clamped to a respective piezo element 20. The mirror 18 may be a rectangular reflector glued at one of its corners 17a with cyanate glue to support disc 121 of piezo electric element 20. The mirror 18 may have a reflection surface of evaporated gold covered by evaporated sapphire. The support disc 121 may be brass. Behind the support disc 121, a lower part of piezo electric element 20 is clamped by rigid clamp 19. A damping screw 123 is provided off centre of the piezo electric element 20. Damping screw 123 extends through piezo electric element 20 to bear against support disc 21 through a damping medium 125. The damping medium may conveniently be felt or leather. When the piezo element is actuated to vibrate, vibrations are transmitted to the mirror with damping through the clamp 119 to cause a rocking, rotating movement of the mirror 18.

FIG. 10B shows a mirror 18 supported on a resilient steel shim which may be, for example, 5/1000 of an inch thick. The shim 200 comprises a first end 201 which is clamped through rigid clamp 219. Mirror 18 is located on a second end 202. The ends 201, 202 are connected through a narrow waist 203. Beneath end 202 a pair of electro-magnets 204 are located to either side of the mirror. A narrow gap 206 is provided between each of the electro-magnets 204a and 204b and the lower surface of the shim 200.

In operation, electro-magnets 204a and 204b are operated out of phase with one another. As each magnet attracts end 202 of shim 200, a twisting movement at waist 203 is achieved. Mirror 18 therefore describes a rocking/rotating movement to cause a beam of light reflected from it to describe a closed curve such as a circle or an ellipse.

FIG. 10C illustrates a digital projection display system comprising a mosaic of mirrors 18. This system of particular interest for large egg handling operations where more than one line of eggs may be used.

Each mirror in the array 300 of mirrors is suspended above an individual SRAM cell by two thin metal torsion hinges 301. Electro-static forces are created between the mirrors and address electrodes 302 connected to the SRAM nodes appear. These forces twist the mirrors one way or the other about an axis through the torsion hinges until the rotation is stopped at a precise angle determined by one mirror edge or the other touching the underlying substrate. Such a digital display system is manufactured by Texas Instruments.

Figure 11:
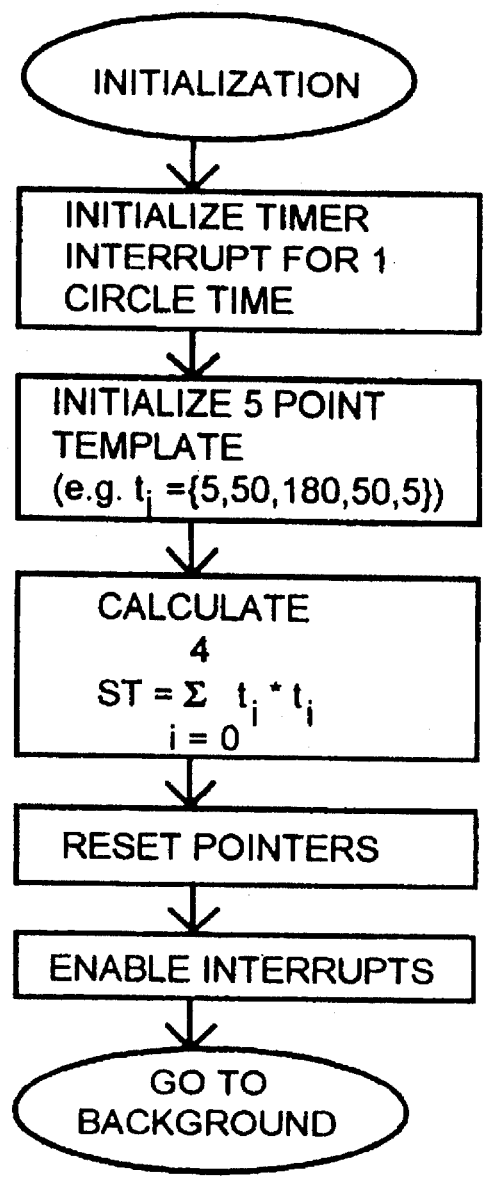
FIG. 11 is a flow diagram of initialization procedures.

FIG. 11 is a flow chart of the initialization procedure for the lasers 14. Firstly the timer interrupt for one circle timer is initialized and then a template is formed for the circles. Correlation integration and match filtering are used to detect crack signatures. The template may be from 3 to 11 samples for length. Conveniently the template may be 5 points with an interval i therebetween. The template is stored as $t_i$, i being equal to 0 to 4. The points of the circle may be set at, for example, 5, 50, 180, 50 and 5. It is then possible to calculate the settings according to the formula:

$$\text{CALCULATE } ST = \sum_{i=0}^{4} t_i * t_i$$

The pointers can then be reset and the interrupts enabled. It is to be noted that the calculation using a 5 point template is for convenience only. A nine point or other template may alternatively be used.

Figure 12A:
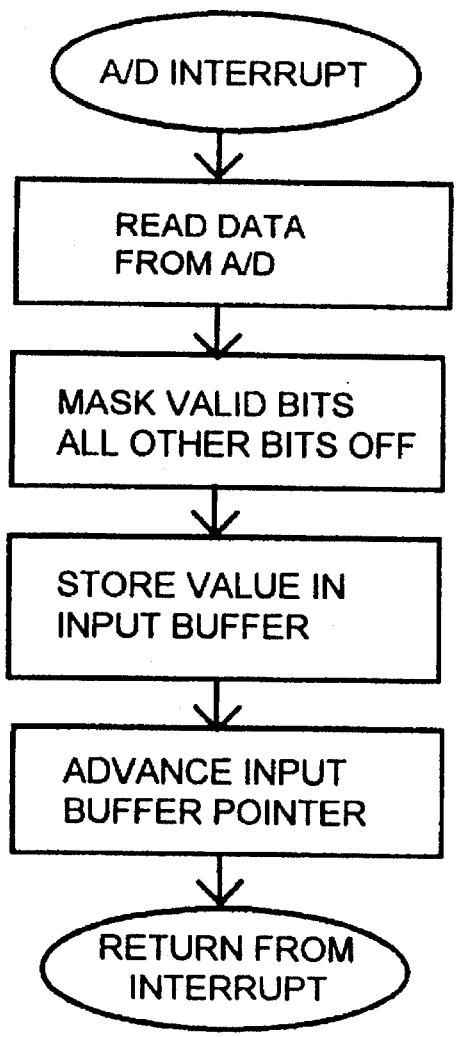
FIGS. 12A and 12B are a flow diagrams of the interrupts for data collection by the photo detector and for setting the flag for another ellipse.
Figure 12B:
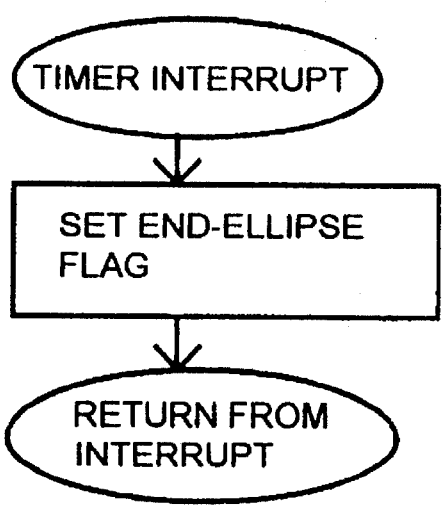

FIG. 12A is a flow chart showing the acquisition of data from the photo detector 24 by the analogue digitiser 30. The analogue digitiser interrupt may, for example, be approximately 250,000 times per second.

Figure 13A:
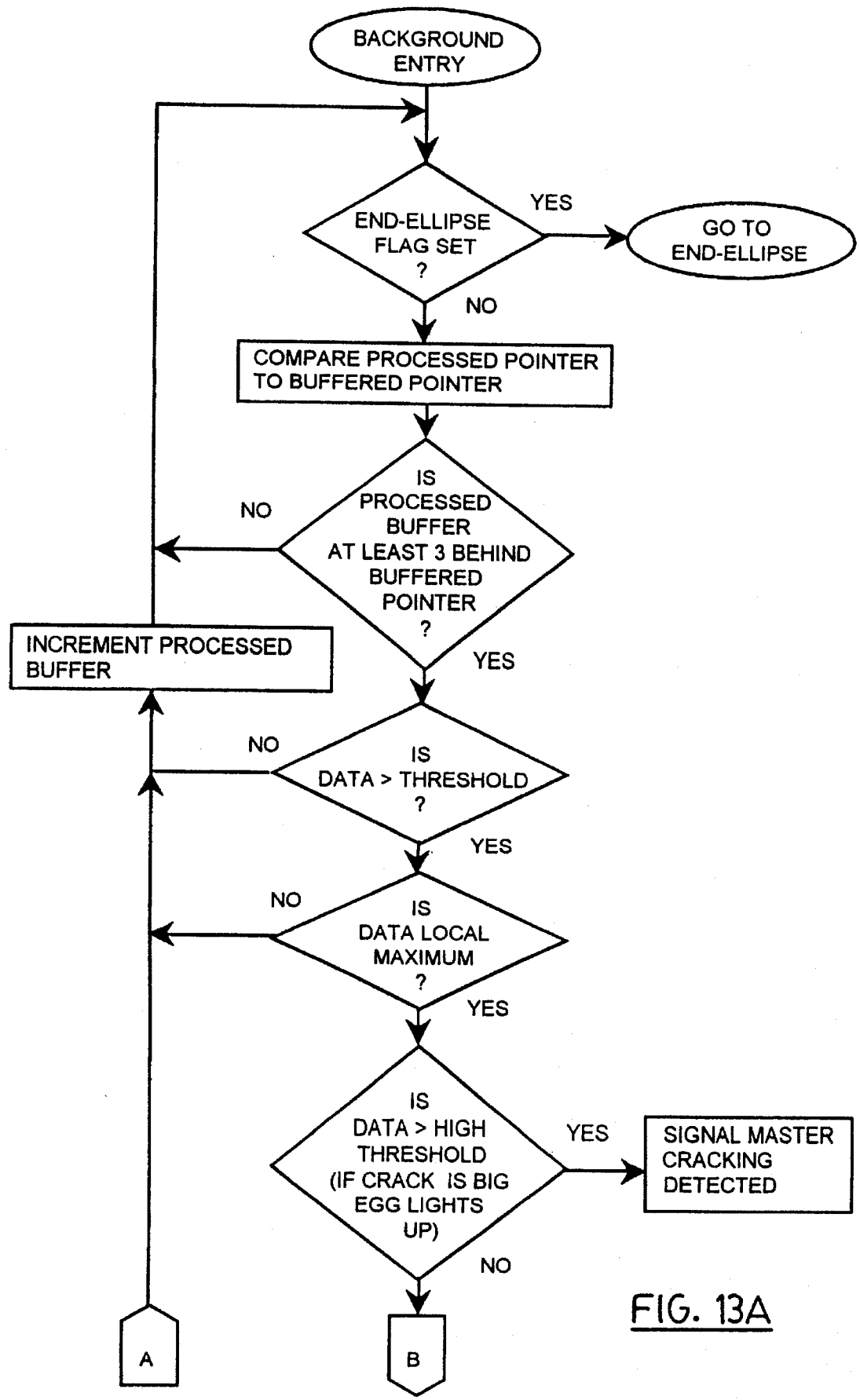
FIGS. 13A and 13B are a flow diagram of the main program for detecting flaws and distinguishing the type of flaw.
Figure 13B:
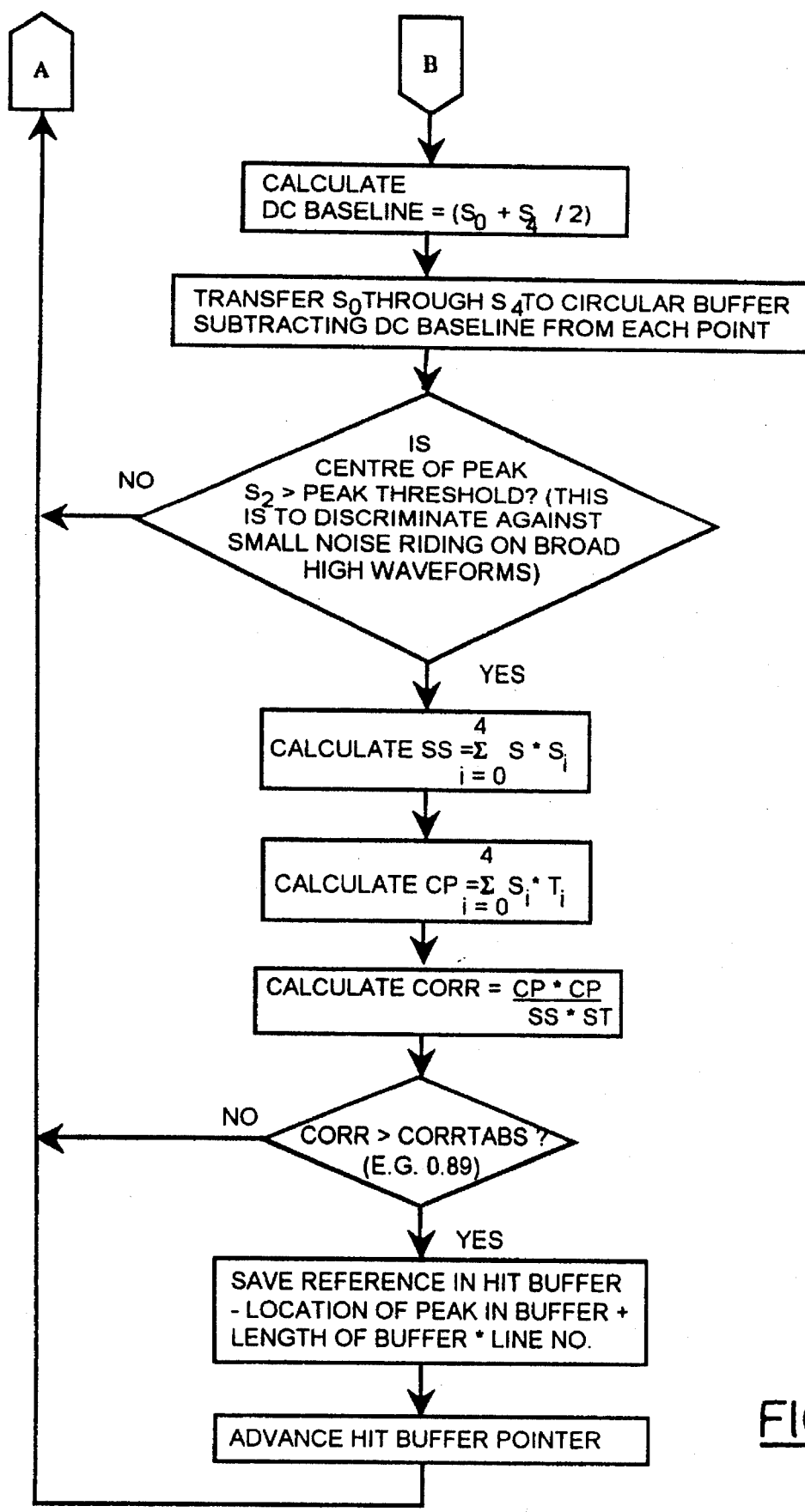

FIG. 13 is a flow chart of the main program of the digital signal processor indicating the procedure for detecting and distinguishing the type of flaws in an egg.

Figure 14A:
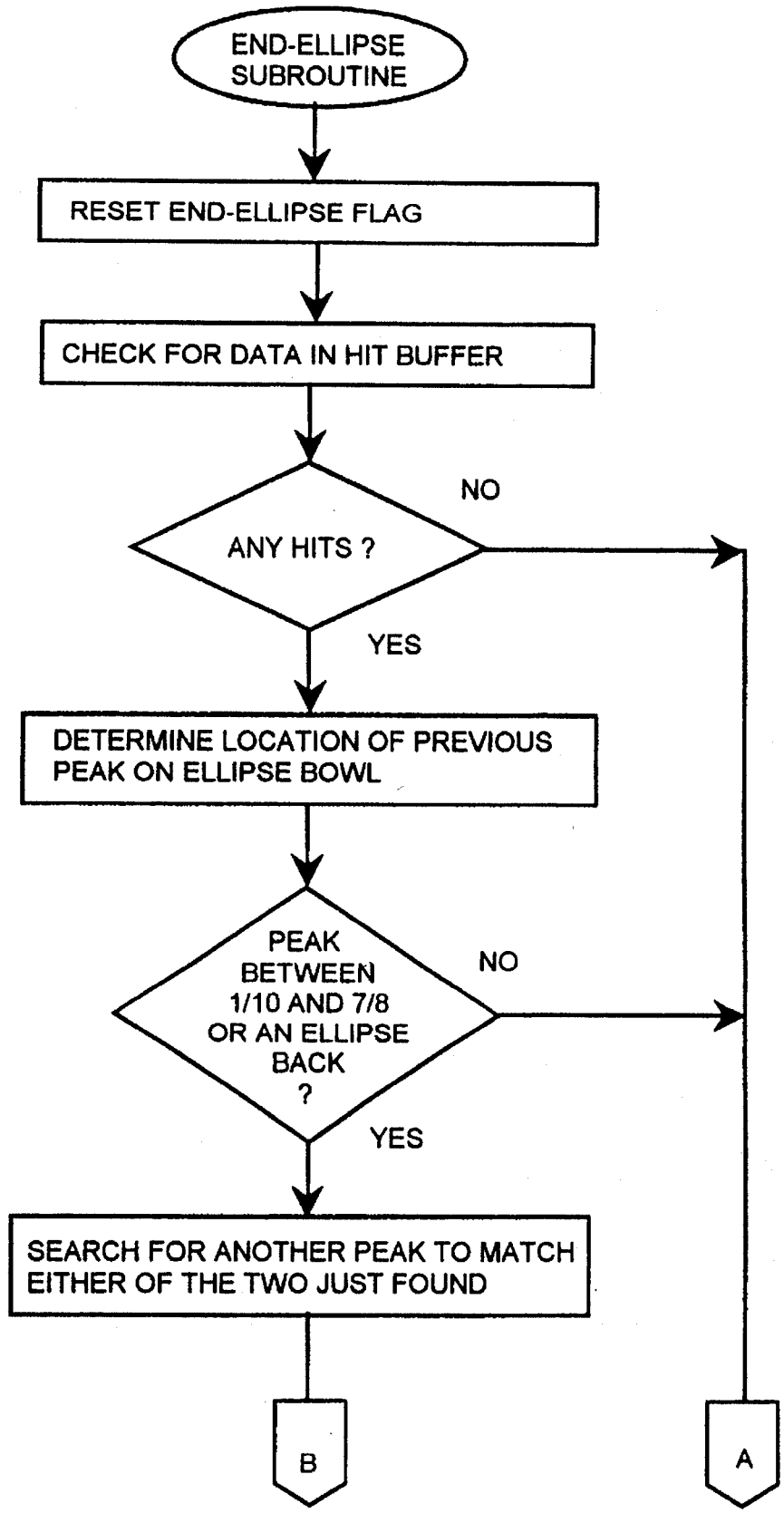
FIGS. 14A and 14B are a flow diagram of the program for ending an ellipse and rejecting an egg.
Figure 14B:
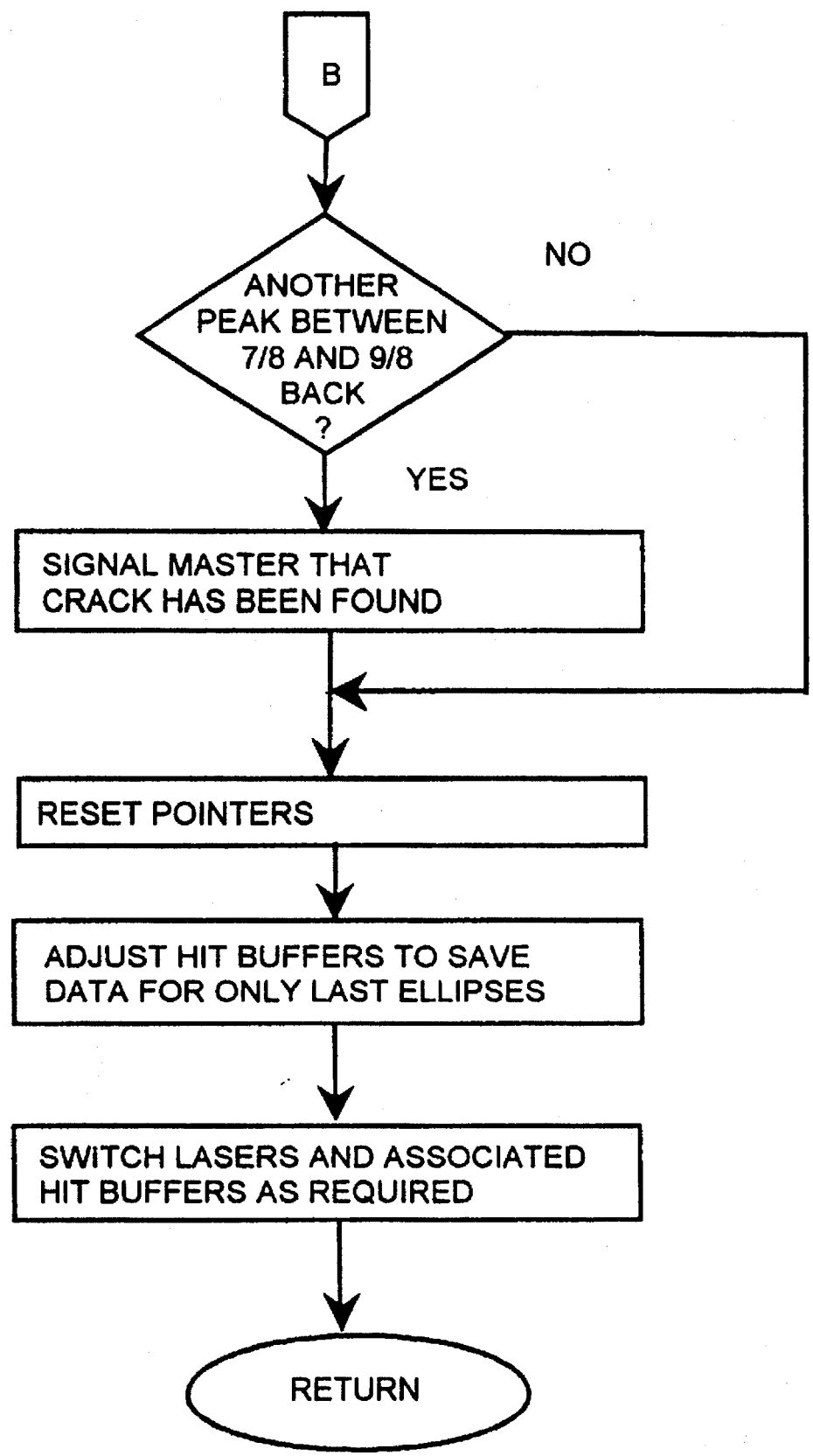

The flow charts of FIG. 13 and 14 are largely self explanatory. The template settings ST have been calculated in the initialization procedures as set out above. The buffered values are calculated from the formula:

$$\text{CALCULATE } SS = \sum_{i=0}^{4} S * S_i$$

The cross product may then be calculated from $$\text{CALCULATE } CP = \sum_{i=0}^{4} S_i * T_i$$

and, eventually the correlation coefficient is calculated from $$\text{Correlation Coefficient} = \frac{CP \times CP}{SS \times ST}$$

While the apparatus and systems have generally been described in relation to a single sequence of eggs advancing through the system. It will be appreciated, as shown in FIG. 2, that the sequences of eggs may be arranged in rows. Six rows may be a convenient number for the operation of some egg candling equipment but more or less rows are possible. Indeed 18 rows may be convenient in some operations.

We claim:

1. Apparatus for detecting flaws in eggs and for distinguishing between flaws in different natures, the apparatus comprising:
   a) means to rotate the egg about its longitudinal axis;
   b) means to form at least one laser beam and focus it to a spot focus;
   c) means to vibrate the laser beam at a speed and amplitude such that the spot focus appears as a geometric figure selected from closed curves and straight lines;
   d) means to direct the at least one laser beam to scan the egg along at least one circumferential path thereabout during at least one revolution of the egg with said at least one vibrating laser beam such that sequential geometric figures of the laser beam overlap one another along the circumferential path;
   e) detection means to detect peaks in intensity in light emanating from the egg;
   f) signal processing means to develop a progression of signals corresponding to the number, size and character of said peaks in intensity of said light emanating from the egg;
   g) computer means to process said signals and to deduce, from the number, size and character of the peaks in intensity, the nature of a flaw in the egg.

2. Apparatus as claimed in claim 1 in which the means to rotate the egg about its longitudinal axis includes a preliminary conveyor having spool rollers to impart preliminary spin to the egg and a secondary conveyor having means to increase the preliminary spin to a prechosen designed spin speed.

3. Apparatus as claimed in claim 2 in which the secondary conveyor includes a ramp down which the eggs roll and driven support strings for the egg longitudinal of the ramp to impart spin to the eggs through friction therewith.

4. Apparatus as claimed in claim 3 in which means are provided to segregate and control rolling speed of eggs on the ramp.

5. Apparatus as claimed in claim 1 in which means are provide to form a first beam and the vibrating means are provided to act on the first beam to form the vibrating beam therefrom.

6. Apparatus as claimed in claim 5 in which the means to form the first beam is a semi-conductor laser.

7. Apparatus as claimed in claim 5 in which the vibrating means is a mirror rotatably vibrated by a piezo electric element, the mirror being clamped to the piezo electric element through, on the one hand a rigid clamp and, on the other hand, through an eccentrically positioned damping mechanism.

8. Apparatus as claimed in claim 5 in which the vibrating means is a mirror rotatably vibrated by means of electromagnetic vibrations.

9. Apparatus as claimed in claim 1 in which the vibrating light beam is formed and vibrated simultaneously by means of directing a diffused beam of light to be reflected as discrete light beams from a digital micro-mirror display device of which individual mirrors are programmed to perform a rotational twisting movement.

10. Apparatus as claimed in claim 1 in which the computer means comprises at least one digital signal processor.

11. Apparatus as claimed in claim 1 in which the computer means includes means to identify flaws through identification of characteristics of a digitized progression of signals from the detection means.

12. Apparatus as claimed in claim 11 including means to reject flawed eggs.

13. A process for detecting flaws in eggs and deducing their nature comprising the steps of:

a) rotating the egg about its longitudinal axis;

b) forming a laser beam and focusing it to a spot focus;

c) vibrating the laser beam at a speed and amplitude so that the spot focus appears as a geometric figure selected from closed curves and straight lines;

d) scanning the egg along at least one circumferential path about the egg in at least one revolution of the egg with said at least one vibrating laser beam such that sequential geometric figures of the laser beam overlap one another along the circumferential path;

e) detecting and measuring a number of high intensity values of light emanating from the egg during each description of the geometric figures of the laser beam; and f) deducing from the number character of high intensity values the nature of any flaws which are present.

14. A process as claimed in claim 13 in which the geometric figure is selected from circles and ellipses.

15. A process as claimed in claim 13 which includes the step of increasing the speed of rotation of the egg about its longitudinal axis to a prechosen operational speed.

16. A process as claimed in claim 15 in which the operational speed is from 2 to 5 revolutions per second.

17. A process as claimed in claim 16 in which the operational speed is about 4.5 revolutions per second.

18. A process as claimed in claim 17 in which six, circumferential paths are scanned on each egg.

19. A process as claimed in claim 18 in which each circumferential band has a width of about 2 mm.

20. A process as claimed in claim 18 in which a number of vibrating light beams are provided equal to the number of circumferential paths.

21. A process as claimed in claim 13 in which the closed curve is produced by reflecting light from a mirror vibrating with a twisting movement.

22. A process as claimed in claim 13 in which six circumferential paths are scanned on an egg and the number of laser beams is equal to the number of circumferential paths.

23. A process as claimed in claim 13 in which the laser beam scans more than one of the circumferential paths in sequential revolutions of the egg.

24. A process as claimed in claim 13 in which the laser beam is focused to a spot size of 20 microns to 2,000 microns, preferably to a spot size of 250 microns.

25. A process as claimed in claim 13 in which the laser beam is focused to a spot the size of 250 microns.

26. A process as claimed in claim 13 in which at least one diameter of said geometric figure is about 2 mm.

27. A process as claimed in claim 26 in which the closed curve is an ellipse having a ratio of major to minor axis similar to an aspect ratio for the laser beam.

28. A process as claimed in claim 21 in which said mirror is rocked by vibrating it by means of a piezo electric element, the mirror being attached to said piezo electric element through a first rigid clamp and a second resilient clamp at locations of the mirror such that vibration of the piezo electric element will cause corresponding twisting vibration of the mirror.

29. A process as claimed in claim 21 in which the said at least one vibrating light beam is a laser beam and the mirror is rocked by electromagnetic vibration applied at first and second locations of the mirror.

30. A process as claimed in claim 29 in which the first and second locations are symmetric and the electromagnetic vibrations at each of said first and second locations are out of phase.

31. A process as claimed in claim 13 in which at least one vibrating laser beam is formed and vibrated simultaneously by directing a diffuse laser beam onto a digital micro mirror device to reflectively divide a discrete laser beam from a twistingly vibrating mirror element of the device.

32. A process as claimed in claim 13 including the step of rejecting eggs which have been identified as flawed with flaws of a particular nature.

\* \* \* \* \*